United States Patent [19]

Saito et al.

[11] Patent Number: 4,535,076
[45] Date of Patent: Aug. 13, 1985

[54] ORGANOPHOSPHATE PESTICIDES

[75] Inventors: Junichi Saito, Tokyo; Akio Kudamatsu, Kanagawa; Toyohiko Kume; Shinichi Tsuboi, both of Tokyo, all of Japan

[73] Assignee: Nihon Tokushu Noyaku Seizo K.K., Tokyo, Japan

[21] Appl. No.: 503,371

[22] Filed: Jun. 10, 1983

[30] Foreign Application Priority Data

Jun. 18, 1982 [JP] Japan .................. 57-103908

[51] Int. Cl.³ .................. A01N 57/14; C07F 9/09; C07F 9/24
[52] U.S. Cl. .................. 514/128; 260/949
[58] Field of Search .................. 260/949; 424/216

[56] References Cited

U.S. PATENT DOCUMENTS 3,755,511  8/1973  McKendry et al. .................. 260/951

FOREIGN PATENT DOCUMENTS 1934001  1/1971  Fed. Rep. of Germany .
2625764  12/1977  Fed. Rep. of Germany .
1173264  2/1959  France .
7809043  10/1978  France .

*Primary Examiner*—Anton H. Sutto
*Attorney, Agent, or Firm*—Sprung, Horn, Kramer & Woods

[57] ABSTRACT

Organophosphate derivatives of the formula

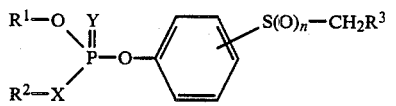

in which
X is O, S or NH,
Y is O or S,
$R^1$ is a lower alkyl group,
$R^2$ is a lower alkyl group or a lower alkoxy-lower alkyl group,
$R^3$ is a fluoro-substituted lower alkyl group, and
n is 0 or 2.

which possess pesticidal properties. The phenols of the phenyl esters are also new.

15 Claims, No Drawings

ORGANOPHOSPHATE PESTICIDES

DETAILED DESCRIPTION OF THE INVENTION

This invention relates to novel organophosphate derivatives, processes for production thereof, and an insecticidal, miticidal or nematocidal agent.

More specifically, this invention relates to novel organophosphate derivatives represented by the following general formula (I)

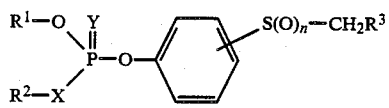
(I)

wherein
X represents O, S or NH,
Y represents O or S,
$R^1$ represents a lower alkyl group,
$R^2$ represents a lower alkyl group or a lower alkoxy-lower alkyl group,
$R^3$ represents a fluoro-substituted lower alkyl group, and
n represents 0 or 2.

The compounds of general formula (I) can be produced, for example, by the following processes to which the invention also pertains.

Process (i)

A process for producing the organophosphate derivatives of general formula (I), which comprises reacting a phosphoric ester halide represented by the general formula

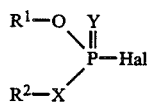
(II)

wherein X, Y, $R^1$ and $R^2$ are as defined above, and Hal represents a halogen atom, with a phenol represented by the general formula

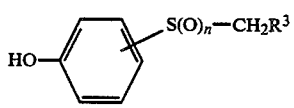
(III)

wherein $R^3$ and n are as defined above.

Process (ii) (X=S)

A process for producing an organophosphate derivative represented by the general formula

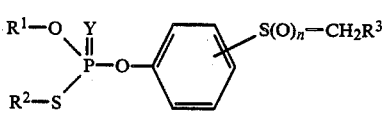
(I')

wherein Y, $R^1$, $R^2$, $R^3$, and n are as defined above, which comprises reacting a phosphoric acid salt represented by the general formula

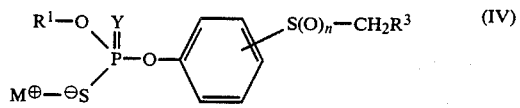
(IV)

wherein Y, $R^1$, $R^3$ and n are as defined, and M represents an alkali metal atom or an ammonium group, with a halide represented by the general formula $R^2$—Hal (V)

wherein $R^2$ and Hal are as defined above.

The organophosphate derivatives of general formula (I) in accordance with this invention can also be produced by the following process (iii), and those derivatives of general formula (I) in which n is 2 can also be produced by the following process (iv).

Process (iii)

A process for producing the organophosphate derivatives of general formula (I), which comprises reacting a phosphoric ester halide represented by the general formula

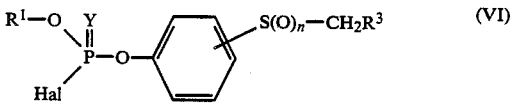
(VI)

wherein Y, $R^1$, $R^3$, n and Hal are as defined above, with a compound represented by the general formula $R^2$—X—H (VII)

wherein X and $R^2$ are as defined above.

Process (iv) (n=2)

A process for producing organophosphate derivatives represented by the following formula

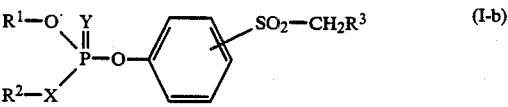
(I-b)

wherein X, Y, $R^1$, $R^2$ and $R^3$ are as defined above, which comprises reacting an organophosphate derivative represented by the general formula

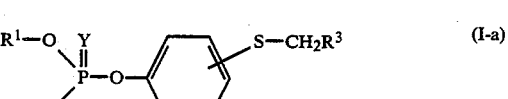
(I-a)

wherein X, Y, $R^1$, $R^2$ and $R^3$ are as defined, with a peroxide.

This invention also relates to an insecticidal, miticidal or nematocidal agent comprising the organophosphate derivative of general formula (I) as an active ingredient.

The invention further relates to the phenol derivative of general formula (III) given above which is an intermediate for the production of the compounds of general formula (I).

The phenol derivative of general formula (III) can, for example, be produced by the following processes (v) and (vi) to which the invention also pertains.

Process (v) (N=0)

A process for producing a phenol derivative represented by the general formula

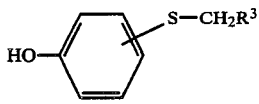
(III-a)

wherein $R^3$ is as defined above, which comprises reacting a sulfonate represented by the general formula

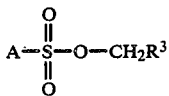
(VIII)

wherein $R^3$ is as defined, and A represents an alkyl or aryl group, with hydroxybenzenethiol represented by the formula:

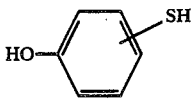
(IX)

Process (vi) (n=2)

A process for producing a phenol derivative represented by the general formula

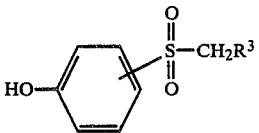
(III-b)

wherein $R^3$ is as defined above, which comprises reacting a phenol derivative represented by the general formula

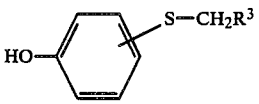
(III-a)

wherein $R^3$ is as defined, with a peroxide.

The specification of U.S. Pat. No. 3,755,511, a publication known before the filing of the present application, discloses that compounds of the following formula (X) have herbicidal, fungicidal and insecticidal activities.

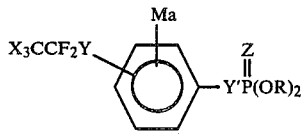
(X)

wherein
each X independently represents hydrogen, bromo, chloro or fluoro, with the proviso that at least one X is always bromo, chloro or fluoro, Y, Y' and Z each independently represent O or S, each M independently represents bromo, chloro, fluoro, iodo, nitro or a lower alkyl group having 1 to 4 carbon atom, a represents 0, 1, 2 or 3, and each R independently represents a lower alkyl group containing 1 to 4 carbon atoms.

The specification of U.S. Pat. No. 4,139,615 (corresponding to Japanese Laid-Open Patent Publication No. 151151/1977) states that compounds of the general formula

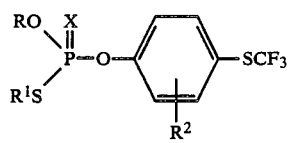
(XI)

wherein R and $R^1$ represent an alkyl group, $R^2$ represents a hydrogen atom or an alkyl group, and X represents an oxygen or sulfur atom, have insecticidal, miticidal and nematocidal activities.

The present inventors made extensive investigations about organophosphates which are typical insecticidal compounds. These investigations have led to the discovery that novel organophosphate derivatives of general formula (I) not described at all in the literature can be synthesized, and the compounds of formula (I) have unexpectedly excellent biological activities.

The investigations of the present inventors have shown that the active compounds (I) of this invention exhibit an excellent control effect against noxious insects, mites and nematodes in agriculture, forestry and horticulture, and their pest controlling activity technically far surpasses those of the compounds described in the above-cited known publications which seem to be structurally similar to the compounds of this invention.

The greatest characteristic of the compounds of formula (I) of this invention in chemical structure is that as shown clearly by general formula (I), the group —$CH_2R^3$ is substituted on the phenyl group of the O-phenyl ester in the phosphate structure through a sulfur atom or a sulfonyl group, preferably in the 2- or 4-position and particularly preferably in the 4-position of the phenyl group. It has been found that the compounds of this invention represented by general formula (I) and having the aforesaid unique structure can exhibit a hitherto-unobserved surprising control effect against the aforesaid organisms.

The phenol derivatives of general formula (III) are novel compounds not described in known publications, and are industrially useful as intermediates for the production of the novel active compounds of general formula (I) having excellent insecticidal, miticidal and nematocidal activities as described above. The phenol derivatives (III) of the invention are also expected as intermediates for other biologically active substances such as medicines.

It is an object of this invention therefore to provide the novel organophosphate derivatives of general formula (I), the novel phenol derivatives of general formula (III) as intermediates for the organophosphate derivatives of general formula (I), processes for the production of these derivatives, and their use as an insecticidal, miticidal or nematocidal agent.

The above and other objects of this invention along with its advantages will become more apparent from the following description.

The active compounds of this invention exhibit an accurate control effect against noxious insects, mites and nematodes without causing any phytotoxicity to cultivated crops. Furthermore, the compounds of this invention can be used for the controlling and combatting of a wide variety of pests including noxious sucking and biting insects, other plant parasites, stored grain pests, and pests significant in the field of hygiene.

Examples of these pests include insects, for example coleopterous insects such as *Callosobruchus chinensis, Sitophilus zeamais, Tribolium castaneum, Epillachna vigintioctomaculata, Agriotes fuscicollis, Anomala rufocuprea, Leptinotarsa decemlineata, Diabrotica* spp., *Monochamus altarnatus* and *Lyctus brunneus*, lepidopterous insects such as *Lymantria dispar, Malacosoma neustria, Pieris rapae, Spodoptera litura, Mamestra brassicae, Chilo suppressalis, Pyrausia nubilalis, Ephestia cautella, Adoxophyes orana, Carpocapsa pomonella, Galleria mellonella,* and *Phyllocnistis citrella*, hemipterous insects such as *Nephotettix cincticeps, Nilaparvata lugens, Pseudococcus comostocki, Unaspis yanonensis, Myzus persicae, Aphis pomi, Rhopalosiphum pseudobrassicas, Stephanitis nashi, Nazara* spp., *Cimex lectularius, Trialeurodes vaporariorum,* and *Psylla* spp., orthopterous insects such as *Blatella germanica, Periplaneta americana, Gryllotalpa africana* and *Locusta migratoria migratoriodes*, isopterous insects such as *Deucotermes speratus* and *Coptotermes formosanus*, and dipterous insects such as *Musca domestica, Aedes aegypti, Hylemia platura, Culex pipiens, Anopheles sinensis* and *Culex tritaeniorhynchus;* mites such as *Tetranychus telarius, Panonychus citri, Aculus pelekassi* and *Torronomus* spp.; and nematodes such as *Meloidogyne incognita, Bursaphelenchus lignicolus Mamiya et Kiyohara, Aphelenchoides besseyi, Heterodera glycines* and *Pratyleochus* spp.

In the field of veterinary medicine, the novel compounds of this invention can be effectively used against various animal parasites (endo- and ecto-parasites) such as ticks, insects and worms. As illustrative of such ticks, there can be mentioned *Oranithodoros* spp., *Ixodes* spp. and *Boophilus* spp., and illustrative of the insects are *Gastrophilus* spp., *Stomoxys* spp., *Trichodectes* spp., *Rhodnius* spp. and *Ctenocephalidex canis*.

In the present invention, substances having the action of controlling and killing all of these pests may sometimes be referred to generically as pesticides.

The compound of formula (I) of this invention can be produced, for example, by the following processes.

Process (i)

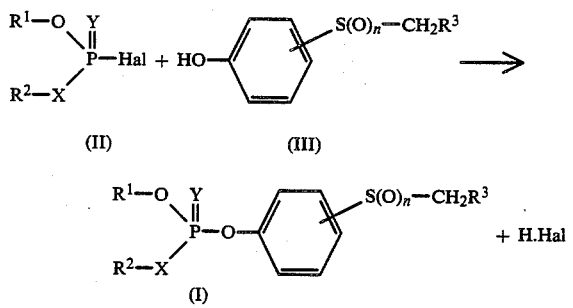

(In the formulae, X, Y, $R^1$, $R^2$, $R^3$ and n are as defined hereinabove.)

In the above reaction scheme:
X represents O, S or NH;
Y represents O or S;
$R^1$ represents a lower alkyl group, for example an alkyl group having 1 to 4 carbon atoms such as methyl, ethyl, propyl, isopropyl, and n-(iso-, sec, or tert-)butyl;

$R^2$ represents a lower alkyl group, or a lower alkoxy-lower alkyl group, for example the same lower alkyl group as exemplified above, or the same lower alkyl group as exemplified above which is substituted by a lower alkoxy group having the same lower alkyl group as exemplified above;

$R^3$ represents a fluoro-substituted lower alkyl group, for example the same lower alkyl group as exemplified above which is substituted by a fluorine atom;

n represents 0 or 2; and

Hal represents a halogen atom such as fluoro, chloro, bromo or iodo, preferably chloro, bromo and iodo.

Specific examples of the phosphoric ester halide of general formula (II) used as a starting material in the process for producing the compounds of this invention shown by the above reaction scheme include
O-ethyl-S-propyl-thiophosphate chloride,
O-ethyl-S-propyl-dithiophosphate chloride,
O,O-diethyl-thiophosphate chloride,
O,O-dimethyl-thiophosphate chloride,
O-ethyl-S-sec-butyl-thiophosphate chloride,
O-ethyl-S-ethoxyethyl-thiophosphate chloride,
O-ethyl-N-isopropylamidothiophosphate chloride and also include the corresponding bromides taking the place of the above phosphoric acid ester chlorides.

Examples of the phenol of general formula (III) which are likewise a starting material include
4-(2,2,2-trifluoroethylthio)phenol,
2-(2,2,2-trifluoroethylthio)phenol,
4-(2,2,2-trifluoroethylsulfonyl)phenol,
4-(2,2,3,3-tetrafluoropropylthio)phenol,
2-(2,2,3,3-tetrafluoropropylthio)phenol,
4-(2,2,3,3,3-pentafluoropropylthio)phenol,
4-(2,2,3,3-tetrafluoropropylsulfonyl)phenol.

By citing a typical example, the above manufacturing process will be specifically described.

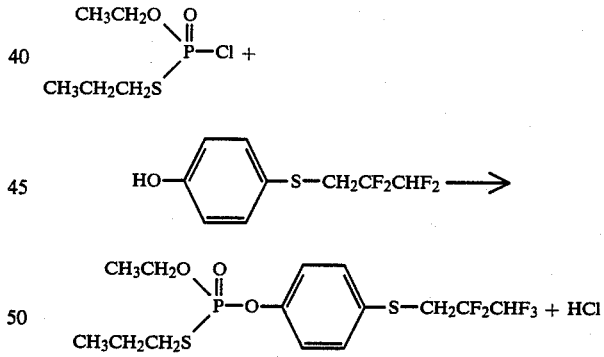

The process for producing the active compounds of this invention can be carried out desirably by using a solvent or diluent. For this purpose, all inert solvents and diluents can be used.

Examples of such solvents or diluents include water; aliphatic, alicyclic and aromatic hydrocarbons (which may optionally be chlorinated) such as hexane, cyclohexane, petroleum ether, ligroin, benzene, toluene, xylene, methylene chloride, chloroform, carbon tetrachloride, ethylene chloride, trichloroethylene and chlorobenzene; ethers such as diethyl ether, methyl ethyl ether, diisopropyl ether, dibutyl ether, propylene oxide, dioxane and tetrahydrofuran; ketones such as acetone, methyl ethyl ketone, methyl isopropyl ketone, and methyl iso-butyl ketone; nitriles such as acetonitrile, propionitrile and acrylonitrile; alcohols such as methanol, ethanol, isopropanol, butanol and ethylene glycol; esters such as ethyl acetate and amyl acetate; acid amides such as dimethylformamide and dimethylacetamide; sulfones and sulfoxides such as dimethyl sulfoxide and sulfolane; and bases such as pyridine.

The reaction of this invention can be carried out in the presence of an acid binder. Examples of the acid binder are the hydroxides, carbonaates, bicarbonates and alcoholates of alkali metals, and tertiary amines such as triethylamine, diethylaniline and pyridine, which are commonly used.

The process of this invention can be carried out over a broad temperature range, generally at a temperature between about −20° C. and the boiling point of the mixture, desirably at a temperature between about 0° and about 100° C. Desirably, the reaction is carried out under atmospheric pressure, but it is also possible to operate under elevated or reduced pressures.

Process (ii) (X=S)

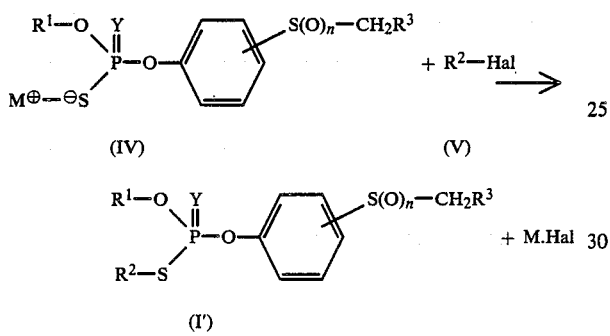

(In the formulae, Y, R$^1$, R$^2$, R$^3$, n, Hal and M are as defined above.)

In the above reaction scheme, examples of Y, RHU 1, R$^2$, R$^3$, n and Hal are the same as those exemplified hereinabove.

Examples of M include alkali metal atoms such as lithium, potassium and sodium, and an ammonium group.

Specific examples of the phosphoric acid salt of general formula (IV) which are a starting material in the process shown by the above reaction scheme include
potassium O-ethyl-O-[4-(2,2,2-trifluoroethylthio)phenyl]thiophosphate,
potassium O-ethyl-O-[2-(2,2,2-trifluoroethylthio)phenyl]thiophosphate,
Potassium O-ethyl-O-[4-(2,2,3,3-tetrafluoropropylthio)phenyl]thiophosphate,
potassium O-ethyl-O-[4-(2,2,3,3,3-pentafluoropropylthio)phenyl]thiophosphate,
potassium O-ethyl-O-[2-(2,2,3,3-tetrafluoropropylthio)phenyl]thiophosphate,
potassium O-ethyl-O-[4-(2,2,2-trifluoroethylsulfonyl)phenyl]thiophosphate, and
potassium O-ethyl-O-[4-(2,2,3,3-tetrafluoropropylsulfonyl)phenyl]thiophosphate.

The corresponding alkali metal salts, specifically lithium or sodium salts, and ammonium salts can also be cited in addition to the potassium salts.

Examples of the halide of general formula (V) which are likewise a starting material include propyl bromide, sec-butyl bromide and 2-ethoxyethyl bromide. The corresponding chlorides can also be cited.

By citing a typical example, the above manufacturing process will be specifically described.

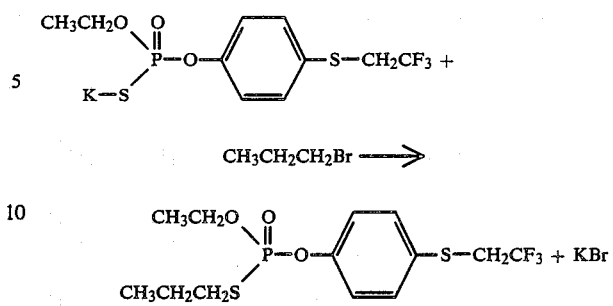

The above process can be carried out over a broad temperature range using the same inert solvent or diluent as exemplified hereinabove. The reaction can be carried out generally at a temperature between about −20° C. and the boiling point of the mixture, desirably at a temperature between about 0° and about 100° C. The reaction is carried out desirably under atmospheric pressure, but it is also possible to operate under elevated or reduced pressure.

Process (iii)

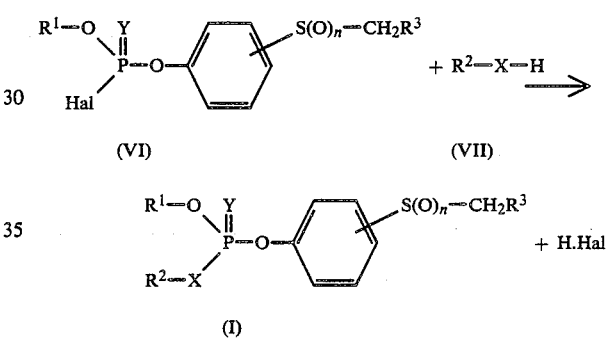

(In the formulae, X, Y, R$^1$, R$^2$, R$^3$, n and Hal are as defined above.)

In the reaction scheme, examples of X, Y, R$^1$, R$^2$, R$^3$, n and Hal may be the same as exemplified hereinabove.

Specific examples of the phosphoric ester halide of general formula (VI) which are a starting material in the process shown by the above reaction scheme include
O-ethyl-O-[4-(2,2,2-trifluoroethylthio)phenyl]phosphate chloride,
O-methyl-O-[4-(2,2,2-trifluoroethylthio)phenyl]phosphate chloride,
O-ethyl-O-[4-(2,2,3,3-tetrafluoropropylthio)phenyl]phosphate chloride,
O-ethyl-O-[2-(2,2,2-trifluoroethylthio)phenyl]phosphate chloride,
O-ethyl-O-[2-(2,2,3,3-tetrafluoropropylthio)phenyl]phosphate chloride,
O-ethyl-O-[4-(2,2,2-trifluoroethylsulfonyl)phenyl]phosphate chloride,
O-ethyl-O-[4-(2,2,3,3,3-pentafluoropropylthio)phenyl]phosphate chloride, and
O-ethyl-O-[4-(2,2,3,3-tetrafluoropropylsulfonyl)phenyl]phosphate chloride.

In addition to the above phosphate chlorides, the corresponding thiophosphate chlorides can also be cited. The corresponding bromides can also be cited as examples.

Specific examples of the compound of general formula (VII) which are likewise a starting material include
methanol,
ethanol,
ethanethiol,
propanol,
propane-1-thiol,
butane-2-thiol,
2-ethoxyethane thiol, and
isopropylamine.

An example of the above process is shown below.

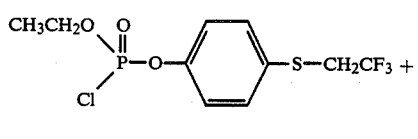

CH₃CH₂CH₂SH ⟶

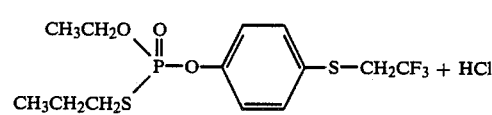

The above process can be carried out over a broad temperature range using the same inert solvents or diluents as exemplified above excepting water and alcohols. The reaction can be carried out generally at a temperature between about −20° C. and the boiling point of the mixture, desirably at a temperature between about 0° and about 100° C. The reaction is carried out desirably under atmospheric pressure, but it is also possible to operate under elevated or reduced pressures.

The above reaction can be carried out in the presence of the same acid binders as exemplified hereinabove excepting the alcoholates.

Process (iv) (n=2)

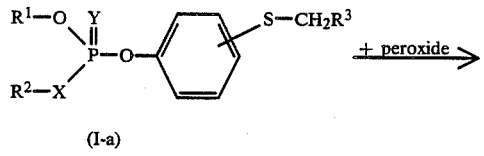

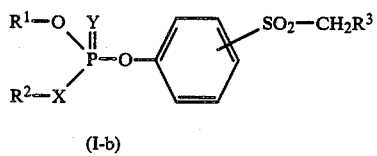

(In the formulae, X, Y, R¹, R², and R³ are the same as defined hereinabove.)

In the above reaction scheme, examples of X, Y, R¹, R² and R³ may be the same as those exemplified hereinabove.

The compounds of general formula (I-a) are embraced within the compounds of general formula (I) of this invention. One example is O,O-diethyl-O-[4-(2,2,2-trifluoroethylsulfonyl)phenyl]thiophosphate.

In the above reaction scheme, specific examples of the peroxide are m-chloroperbenzoic acid and hydrogen peroxide.

The above process can be carried out over a broad temperature range using the same inert solvents or diluents as exemplified hereinabove. The reaction is carried out generally at a temperature between about −20° C. and the boiling point of the mixture, desirably at a temperature between about 0° and about 100° C. The reaction is carried out desirably under atmospheric pressure, but it is also possible to operate under elevated or reduced pressures.

The phenol derivatives of general formula (III) in accordance with the present invention, intermediates for the production of the compounds of general formula (I), can be produced by the following processes (v) and (vi).

Process (v) (n=0)

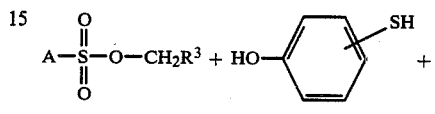

(VIII)    (IX)

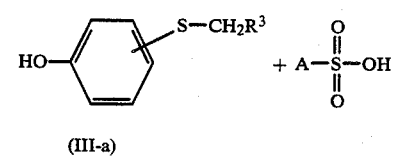

(III-a)

(In the formulae, R³ is as defined above.)

In the above reaction scheme, examples of R³ may be the same as exemplified hereinabove.

Examples of A include not only the same lower alkyl groups as exemplified above with regard to R¹ but also such alkyl groups as n-pentyl, n-hexyl, n-heptyl and n-octyl, and aryl groups such as phenyl, o-(m- or p-)tolyl, 2,3-xylyl, 2,4-xylyl and 2,5-xylyl.

Specific examples of the compound of general formula (VIII) which are a starting material in the process shown by the above reaction scheme include
2,2,2-trifluoroethyl methanesulfonate,
2,2,2-trifluoroethyl p-toluenesulfonate,
2,2,2-trifluoroethyl benzenesulfonate,
2,2,3,3-tetrafluoropropyl p-toluenesulfonate, and
2,2,3,3,3-pentafluoropropyl p-toluenesulfonate.

Specific examples of the hydroxybenzenethiol of formula (IX) which are likewise a starting material are 2-hydroxybenzenethiol and 4-hydroxybenzenethiol.

By citing a typical example, the above manufacturing process will be specifically described.

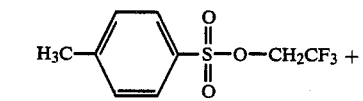

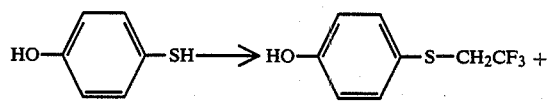

The above process can be carried out in an aprotic polar solvent in the presence of a base such as sodium carbonate, potassium carbonate, sodium hydroxide or potassium hydroxide to give the desired product in high purity and yield. Examples of such a solvent are dimethylformamide, dimethylacetamide, dimethyl sulfoxide, sulfolane, and N-methyl-2-pyrrolidone. Tertiary alcohols, such as tert-butanol, although being protic polar solvents, can be used.

The above process can be carried out over a broad temperature range, generally at a temperature between about −20° C. and the boiling point of the mixture, desirably at a temperature between about 0° and about 100° C. The reaction is carried out desirably under atmospheric pressure, but it is also possible to operate under elevated or reduced pressures.

Process (vi) (n=2)

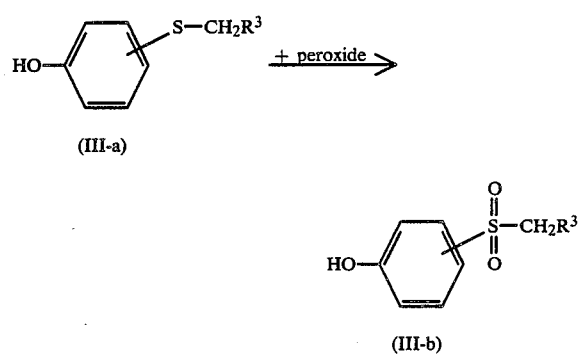

(In the formula, $R^3$ is as defined above.)

Specific examples of the compound of general formula (III-a) in the reaction scheme include
4-(2,2,2-trifluoroethylthio)phenol,
2-(2,2,2-trifluoroethylthio)phenol,
4-(2,2,3,3-tetrafluoropropylthio)phenol,
2-(2,2,3,3-tetrafluoropropylthio)phenol, and
4-(2,2,3,3,3-pentafluoropropylthio)phenol.

Specific examples of the peroxide used in the process shown by the above reaction scheme are m-chloroperbenzoic acid and hydrogen peroxide.

By citing a typical example, the above manufacturing process will be described specifically:

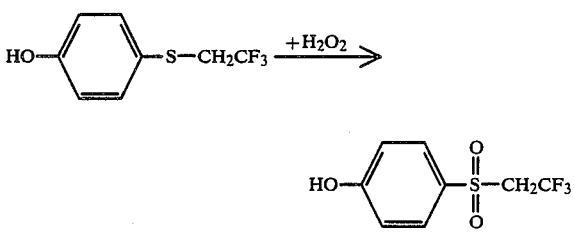

The aforesaid process can be carried out by an ordinary oxidizing technique using the same inert solvents or diluents as described above. The above process can be carried out over a broad temperature range, generally at a temperature between about −20° C. and the boiling point of the mixture, desirably at a temperature between about 0° and about 100° C. The above process is desirably carried out under atmospheric pressure, but it is also possible to operate under elevated or reduced pressure.

In the general formulae lower alkyl $R^1$ means straight chain or branched alkyl with preferably 1 to 6, particularly preferably 1 to 4 carbon atoms, e.g. methyl, ethyl, n.- and i.-propyl, n.-,i.-,s.- and t.-butyl. Particularly preferred are methyl and ethyl.

In the general formulae lower alkyl $R^2$ means straight chain or branched alkyl with preferably 1 to 6, particularly preferred 1 to 4 carbon atoms, e.g. methyl, ethyl, n.- and i.-propyl and n.-,i.-,s.- and t.-butyl. Particularly preferred are methyl, ethyl, n.- and i.-propyl and s.-butyl.

In the general formulae the lower alkoxy lower alkyl group $R^2$ consists of straight chain or branched alkyl and alkoxy parts and contains preferably 1 to 6, particularly preferably 1 to 4 carbon atoms in each of the alkyl and the alkoxy part, e.g. methoxymethyl, ethoxyethyl, methoxyethyl, ethoxyethyl, n.- and i.-propoxyethyl and methoxypropyl.

In the general formulae the fluoro-substituted lower alkyl group $R^3$ is straight chain or branched and has preferably 1 to 6, particularly preferably 1 to 4 carbon atoms. This group is substituted by preferably 1 to 5 and particularly preferably by 1 to 4 fluorine atoms. Examples for this group are the trifluoromethyl group and the 1,1-difluoro-2,2-difluoroethyl group.

In the general formulae the $S(O)_nCH_2$—$R^3$ group is preferably in the 2- or 4-position and particularly in the 4-position of the phenoxy ring and n represents O or 2, preferably O.

Preferred compounds of the formula I are compounds in which $R^1$ represents alkyl with 1 to 4 carbon atoms,
$R^2$ represents alkyl with 1 to 4 carbon atoms, or alkoxyalkyl with 1 to 4 carbon atoms in each of the alkyl and the alkoxy part,
$R^3$ represents fluoro substituted alkyl with 1 to 4 carbon atoms which is substituted by 1 to 4 fluorine atoms,
X represents O, S, or NH,
Y represents S or O and
n represents O or 2.

In these compounds the $S(O)_nCH_2$—$R^3$ group is preferably in the 2 or 4, particularly preferably in the 4 position, of the phenoxy ring.

Particularly preferred are compounds of the formula I, in which
$R^1$ represents methyl or ethyl,
$R^2$ represents methyl, ethyl, n.- and i.-propyl, s.-butyl and ethoxyethyl,
$R^3$ represents trifluoromethyl or 1,1-difluoro-2,2-difluoroethyl,
X represents O, S or NH,
Y represents O or S,
n represents O or 2, especially O and the
$S(O)_nCH_2$—$R^3$ group is in the 2- or 4-(especially in the 4-) position of the phenoxy ring.

For use as an insecticidal, miticidal or nematocidal agent, the active compound of this invention may be used as such after diluting it directly with water, or after formulating it into various forms using agriculturally acceptable adjuvants by methods generally practiced in the production of agricultural chemicals. In actual use, the pesticidal agent in various forms is applied either directly or after diluting it with water to the desired concentrations. Examples of the agriculturally acceptable adjuvants, as referred to herein, are diluents (solvents, extenders, carriers), surface active agents (solubilizing agents, emulsifiers, dispersants, wetting agents), stabilizers, stickers, aerosol propellants, and synergists.

Examples of the solvents are water, and organic solvents, for example hydrocarbons (e.g., n-hexane, petroleum ether, naphtha, petroleum fractions (e.g., paraffin waxes, kerosene, light oils, middle oils, heavy oils), benzene, toluene, and xylenes), halogenated hydrocarbons [e.g., methylene chloride, carbon tetrachloride, trichloroethylene, ethylene chrloride, ethylene dibromide, chlorobenzene and chloroform], alcohols [e.g., methyl alcohol, ethyl alcohol, propyl alcohol, and ethylene glycol], ethers [e.g., ethyl ether, ethylene oxide and dioxane], alcohol ethers [e.g., ethylene glycol monomethyl ether], ketones [e.g., acetone and isophorone], esters [e.g., ethyl acetate and amyl acetate], amides [e.g., dimethylformamide and dimethylacetamide] and sulfoxides [e.g., dimethyl sulfoxide].

Examples of the extenders or carriers include inorganic powders, for example slaked lime, magnesium lime, gypsum, calcium carbonate, silica, perlite, pumice, calcite, diatomaceous earth, amorphous silica, alumina, zeolites, and clay minerals (e.g., pyrophyllite, talc, montmorillonite, beidellite, vermiculite, kaolinite and mica); vegetable powders such as cereal powders, starches, processed starches, sugar, glucose and crushed stalks of plants; and powders of synthetic resins such as phenolic resins, urea resins, and vinyl chloride resins.

Examples of the surface-active agents include anionic surface active agents such as alkylsulfuric acid esters (e.g., sodium laurylsulfate), arylsulfonic acid salts (e.g., alkylarylsulfonic acid salts and sodium alkylnaphthalenesulfonates), succinic acid salts and salts of sulfuric acid esters of polyethylene glycol alkylaryl ethers; cationic surface-active agents such as alkylamines (e.g., laurylamine, stearyl trimethyl ammonium chloride and alkyl dimethylbenzyl ammonium chlorides) and polyoxyethylene alkylamines; nonionic surface-active agents such as polyoxyethylene glycol ethers (e.g., polyoxyethylene alkylaryl ethers and condensation products thereof), polyoxyethylene glycol esters (e.g., polyoxyethylene fatty acid esters), and polyhydric alcohol esters (e.g., polyoxyethylene sorbitan monolaurate); and amphoteric surface-active agents.

Examples of other adjuvants include stabilizers; stickers (e.g., agricultural soaps, casein lime, sodium alginate, polyvinyl alcohol, vinyl acetate-type adhesives, and acrylic adhesives); aerosol propellants (e.g., trichlorofluoromethane, dichlorofluoromethane, 1,2,2-trichloro-1,1,2-trifluoroethane, chlorobenzene, LNG, and lower ethers); combustion controlling agents for fumigation (e.g., nitrites, zinc powder, and dicyandiamide); oxygen-yielding agents (e.g., chlorates and bichromates); phytotoxicity reducing agents (e.g., zinc sulfate, ferrous chloride, and copper sulfate); effect-prolonging agents; dispersion stabilizers (e.g., casein, tragacanth, carboxymethyl cellulose and polyvinyl alcohol); and synergists.

The compounds of this invention can be formulated into various forms by methods generally practiced in the field of manufacturing agricultural chemicals. Examples of the forms include emulsifiable concentrates, oils, wettable powders, soluble powders, suspensions, dusts, granules, pulverulent compositions, fumigants, tablets, pastes, and capsules.

The insecticidal, miticidal or nematocidal agent of this invention may contain about 0.1 to about 95% by weight, preferably about 0.5 to about 90% by weight, of the aforesaid active ingredient.

In actual use, the suitable amount of the active compound in the aforesaid compositions in various forms and ready-to-use preparations is generally about 0.0001 to about 20% by weight, preferably about 0.005 to about 10% by weight.

The content of the active ingredient can be properly varied depending upon the form of the preparation or composition, the method, purpose, time and locus of its application, the state of occurrence of noxious organisms to be controlled, etc.

If required, the compound of this invention may be used further in combination with other agricultural chemicals, for example other insecticides, fungicides, other miticides, other nematocides, antiviral agents, herbicides, plant growth regulators and attractants (e.g., organophosphate compounds, carbamate compounds, dithio(or thiol)carbamate compounds, organochlorine compounds, dinitro compounds, organic sulfur or metal compounds, antibiotics, substituted diphenyl ether compounds, urea compounds, and triazine compounds), and/or fertilizers.

Various compositions and ready-to-use preparations containing the aforesaid active ingredient of the invention can be applied by various methods generally practiced in the field of agricultural chemical application, for example spraying (liquid spraying, misting, atomizing, dusting, granule scattering, water surface application and pouring); fumigation; soil application (mixing, sprinkling, vaporing and injection); surface application (e.g., coating, banding, dust coating, and covering); and dipping. They can also be applied by the so-called ultralow volume spraying method. According to this method, the active ingredient may be included in an amount of 100%.

The rate of application per unit area is about 0.03 to about 10 kg, preferably about 0.3 to about 6 kg, per hectare. In special cases, however, it may, and sometimes should, be outside the specified range.

According to this invention, there is provided an insecticidal, miticidal or nematocidal composition comprising the compound of general formula (I) as an active ingredient and a diluent (a solvent and/or an extender and/or a carrier) and/or a surface-active agent, and if further required, a stabilizer, a sticker, a synergist, etc.

The invention also provides a method for controlling insects, mites and nematodes, which comprises applying to insects, mites and nematodes and/or their habitat or the locus where they are likely to occur the compound of general formula (I) alone or in admixture with a diluent (a solvent and/or an extender and/or a carrier) and/or a surface active agent and if required, a stabilizer, a sticker, a synergist, etc.

The following examples illustrate the present invention specifically. It should be noted however that the invention is not limited to these specific examples alone.

EXAMPLE 1

Wettable powder:

Fifteen parts of compound No. 1 of this invention, 80 parts of a 1:5 mixture of white carbon (a fine powder of hydrous amorphous silicon oxide) and powdery clay, 2 parts of sodium alkylbenzenesulfonate and 3 parts of a sodium alkylnaphthalenesulfonate/formaldehyde condensate are pulverized and mixed to form a wettable powder.

It is diluted with water and sprayed over insects, mites or nematodes and/or their habitat or the locus where they are likely to occur.

EXAMPLE 2

Emulsifiable concentrate:

Thirty parts of compound No. 2 of the invention, 55 parts of xylene, 8 parts of polyoxyethylene alkyl phenyl ether and 7 parts of calcium alkylbenzenesulfonate are mixed with stirring to form an emulsifiable concentrate. It is diluted with water and sprayed onto insects, mites or nematodes and/or their habitat or the locus where they are likely to occur.

EXAMPLE 3

Dust:

Compound No. 3 of the invention (2 parts) and 98 parts of powdery clay are pulverized and mixed to form a dust. It is scattered over insects, mites or nematodes and/or their habitat or the locus where they are likely to occur.

EXAMPLE 4

Dust:

Compound No. 4 of the invention (1.5 parts), 0.5 part of isopropyl hydrogen phosphate (PAP) and 98 parts of powdery clay are pulverized and mixed to form a dust. It is scattered over insects, mites or nematodes and/or their habitat or the locus where they are likely to occur.

EXAMPLE 5

Granules:

Water (25 parts) is added to a mixture consisting of 10 parts of compound No. 5 of the invention, 30 parts of bentonite (montmorillonite), 58 parts of talc and 2 parts of a lignosulfonate, and they are well kneaded. The mixture is processed by an extrusion-type granulating machine to form granules having a size of 10 to 40 mesh which are then dried at 40° to 50° C. to form granules. The granules are scattered over insects, mites or nematodes and/or their habitat or the locus where they are likely to occur.

EXAMPLE 6

Granules:

Ninety-five parts of clay mineral particles having a particle size distribution between 0.2 and 2 mm are put in a rotary mixer, and with rotation, 5 parts of oily compound No. 6 of the invention is sprayed onto the clay mineral particles to cause it to be absorbed uniformly to form granules. They are scattered over insects, mites or nematodes and/or their habitat or the locus where they are likely to occur.

EXAMPLE 7

Oil:

Compound No. 7 of the invention (0.5 part) and 99.5 parts of kerosene are mixed with stirring to form an oil. It is sprayed onto insects, mites or nematodes and/or their habitat or the locus where they are likely to occur.

The unexpected superiority and the marked effects of the active compounds of this invention can be seen from the results of tests shown below in which these compounds were used against various pests including insects, mites and nematodes.

TEST EXAMPLE 1

Test on larvae of *Spodoptera litura:*

Preparation of a test chemical

Solvent: 3 parts by weight of xylene
Emulsifying agent: 1 part by weight of polyoxyethylene alkyl phenyl ether A test chemical preparation was formed by mixing 1 part by weight of a given active compound with the abovementioned solvent and emulsifier in the indicated amounts, and diluting the mixture with water to a predetermined concentration.

Testing method

Sweet potato leaves were dipped in a water dilution of each of the active compounds indicated in Table 1 in a predetermined concentration. After air-drying, the sweet potato leaves were put in a Petri dish having a diameter of 9 cm. Ten 3rd-instar larvae of *Spodoptera litura* were released into the dish. The dish was placed in a constant-temperature chamber at 28° C., and after the lapse of 24 hours, the number of dead insects was examined, and the kill ratio was calculated.

The results are shown in Table 1.

TABLE 1

|  | Concentration of the active ingredient (ppm) | Kill ratio (%) |
| --- | --- | --- |
| Compound No. | | |
| 1 | 10 | 100 |
| 3 | 10 | 100 |
| 4 | 10 | 100 |
| 5 | 10 | 100 |
| 8 | 10 | 100 |
| 9 | 10 | 100 |
| Comparison | | |
| X-1 | 100 | 20 |
| XI-1 | 100 | 90 |
| A | 100 | 50 |

Note
1. The compound numbers correspond to those given in Synthesis Examples and Table 10.
2. Comparison

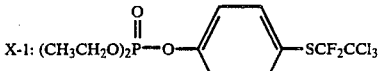

(the compound described in U.S. Pat. Specification No. 3,755,511)

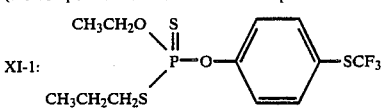

(the compound described in U.S. Pat. Specification No. 4,139,615)

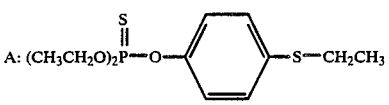

(the compound described in Japanese Patent Publication No. 778/1960)

TEST EXAMPLE 2

Test on *Callosobruchus chinensis:*

Testing method

A filter paper was spread at the bottom of a Petri dish having a diameter of 9 cm, and 1 ml of a water dilution of each of the active compounds shown in Table 2 prepared as in Test Example 1 in a predetermined concentration was put in the dish. Twenty heads of *Callosobruchus chinensis* were released into it, and the Petri dish was placed in a constant temperature chamber at 28° C. After the lapse of 24 hours, the number of dead insects was examined, and the kill ratio was calculated.

The results are shown in Table 2.

TABLE 2

| Compound No. | Concentration of the active ingredient (ppm) | Kill ratio (%) |
| --- | --- | --- |
| 2 | 1 | 100 |
| 3 | 10 | 100 |
| 4 | 10 | 100 |
| 5 | 10 | 100 |
| 6 | 1 | 100 |
| Comparison | | |
| X - 1 | 10 | 0 |
| XI - 1 | 10 | 60 |
| A | 10 | 80 |

Note
1. The compound numbers correspond to Synthesis Examples and Table 10.
2. The compounds used for comparison are the same as in Table 1.

TEST EXAMPLE 3

Test on *Nephotettix cincticeps* having resistance to organophosphate agents:

Testing method

To rice plants, 10 cm in height, planted in pots with a diameter of 12 cm, 10 ml per pot of a water dilution of each of the active compounds indicated in Table 3 in a predetermined concentration prepared as in Test Example 1 was sprayed. After drying the rice plants, a wire cage, 7 cm in diameter and 14 cm in height, was put over the plants, and 30 female imagoes of *Nephotettix cincticeps* showing resistance to organophosphate agents were released into the cage. After standing for 24 hours in a constant-temperature chamber, the number of dead insects was examined, and the kill ratio was calculated.

The results are shown in Table 3.

TABLE 3

| Compound No. | Concentration of the active ingredient (ppm) | Kill ratio (%) |
| --- | --- | --- |
| 3 | 10 | 100 |
| 4 | 10 | 100 |
| 8 | 100 | 100 |
| 9 | 100 | 100 |
| 13 | 100 | 100 |
| Comparison | | |
| X - 1 | 100 | 50 |
| XI - 1 | 100 | 0 |
| A | 100 | 0 |

Note
1. The compound numbers correspond to those given in Table 10.
2. The compounds used for comparison were the same as in Table 1.

TEST EXAMPLE 4

Test on *Musca domestica*:

Testing method

A filter paper was spread at the bottom of a Petri dish having a diameter of 9 cm, and 1 ml of a water dilution of each of the active compounds indicated in Table 4 in a predetermined concentration prepared as in Test Example 1 was put into the dish. Ten female imagoes of *Musca domestica* having resistance to commercial organophosphate agents were released into the dish. The dish was placed in a constant-temperature chamber at 29° C. After the lapse of 24 hours, the number of dead insects was examined, and the kill ratio was calculated.

The results are shown in Table 4.

TABLE 4

| Compound No. | Concentration of the active ingredient (ppm) | Kill ratio (%) |
| --- | --- | --- |
| 3 | 100 | 100 |
| 4 | 100 | 100 |
| Comparison | | |
| X - 1 | 100 | 0 |
| XI - 1 | 100 | 0 |
| A | 100 | 0 |

Note
1. The compound numbers correspond to those given in Table 10.
2. The compounds used for comparative purposes are the same as those given in Table 1.

TEST EXAMPLE 5

Test on *Tetranychus telarius*:

Fifty to 100 imagoes of *Tetranychus telarius* having resistance to organophosphate agents were inoculated in the leaves of kidney beans (*Phaseolus vulgaris* Linn.) in the stage of developing two main leaves, which were grown in pots having a diameter of 6 cm. Two days later, a water dilution of each of the active compounds shown in Table 5 in a predetermined concentration prepared as in Test Example 1 was sprayed in an amount of 40 ml per pot. The pots were placed in a greenhouse, and after the lapse of 10 days, the control effect of the active compound was evaluated and shown by indices. The indices mean the following.

3: the proportion of surviving imagoes was 0%.
2: the proportion of surviving imagoes was more than 0% but less than 5% based on a non-treated area.
1: the proportion of surviving imagoes was 5 to 50% based on the non-treated area.
0: the proportion of surviving imagoes was more than 50% based on the non-treated area.

The results are shown in Table 5.

TABLE 5

| Compound No. | Concentration of the active ingredient (ppm) | Control index |
| --- | --- | --- |
| 1 | 100 | 3 |
| 3 | 100 | 3 |
| 4 | 100 | 3 |
| 5 | 100 | 3 |
| 8 | 100 | 3 |
| 9 | 100 | 3 |
| 12 | 100 | 3 |
| 13 | 100 | 3 |
| Compound | | |
| X - 1 | 100 | 0 |
| XI - 1 | 100 | 0 |
| A | 100 | 0 |

Note
1. The compound numbers correspond to those given in Synthesis Examples and Table 10.
2. The compounds used for comparison are the same as those given in Table 1.

TEST EXAMPLE 6

Test on *Blatella germanica*:

Testing method

A filter paper was spread at the bottom of a Petri dish having a diameter of 9 cm, and 1 ml of a water dilution of each of the active compounds indicated in Table 6 in a predetermined concentration prepared as in Test Example 1 was put in it. Ten imagoes of *Blatella germanica* were released into the dish. The dish was placed in a constant-temperature chamber at 28° C. After the lapse of 24 hours, the number of dead insects was examined, and the kill ratio was calculated.

The results are shown in Table 6.

TABLE 6

| | Concentration of the active ingredient (ppm) | Kill ratio (%) |
|---|---|---|
| Compound No. | | |
| 2 | 10 | 100 |
| 4 | 100 | 100 |
| 6 | 10 | 100 |
| 7 | 100 | 100 |
| 10 | 100 | 100 |
| 11 | 100 | 100 |
| Comparison | | |
| X - 1 | 100 | 80 |
| XI - 1 | 100 | 10 |
| A | 100 | 0 |

Note
1. The compound numbers correspond to those given in Synthesis Examples and Table 10.
2. The compounds used for comparison are the same as those given in Table 1.

TEST EXAMPLE 7

Test on larvae of *Culex pipiens*:

Testing method

One hundred milliliters of a water dilution of each of the active compounds shown in Table 7 in a predetermined concentration prepared as in Test Example 1 was put in a deep Petri dish having a diameter of 9 cm, and 25 4-instar larvae of *Culex pipiens* were released into the dish. The dish was placed in a constant temperature chamber at 28° C. After the lapse of 24 hours, the number of dead insects was examined, and the kill ratio was calculated. The results are shown in Table 7.

TABLE 7

| | Concentration of the active ingredient (ppm) | Kill ratio (%) |
|---|---|---|
| Compound No. | | |
| 1 | 0.1 | 100 |
| 2 | 0.001 | 100 |
| 3 | 0.1 | 100 |
| 4 | 0.01 | 100 |
| 6 | 0.01 | 100 |
| 7 | 0.1 | 100 |
| 9 | 0.01 | 100 |
| 10 | 0.01 | 100 |
| 11 | 0.1 | 100 |
| 12 | 0.1 | 100 |
| 13 | 0.01 | 100 |
| Comparison | | |
| X - 1 | 0.1 | 40 |
| XI - 1 | 0.1 | 70 |
| A | 0.1 | 70 |

Note
1. The compound numbers correspond to those given in Synthesis Examples and Table 10.
2. The compounds for comparison are the same as those given in Table 1.

TEST EXAMPLE 8

Test on *Meloidogyne incognita*:

Preparation of a test chemical

Two parts of each of the active compounds shown in Table 8 and 98 parts of talc were pulverized and mixed.

Testing method

The test chemical prepared as above was added to the soil infected by *Meloidogyne incognita* in such an amount as to provide a concentration of 50 ppm, 25 ppm, 10 ppm and 5 ppm, respectively. They were mixed uniformly with stirring and then charged into pots each of 1/5000 are. In the charged mixture were sown about 20 seeds of tomato (variety: KURIHARA) per pot. The tomato seeds were cultivated in a greenhouse. Four weeks later, the grown roots were pulled out with care taken not to damage them and the degree of injury of 10 roots at random was evaluated based on the following ratings and a root-knot index was determined.

Degree of injury

0 ... no root-knot formation (perfect control)
1 ... slight root-knot formation
3 ... strong root-knot formation
4 ... strongest root-knot formation (corresponding to non-treatment)

$$\text{Root-knot index} = \frac{\Sigma(\text{rating} \times \text{number of roots})}{(\text{total number of examined roots}) \times 4} \times 100$$

From above, the following control effect was obtained:

$$\text{Control effect} = \frac{\substack{(\text{root-knot index} \\ \text{of untreated plot})} - \substack{(\text{root-knot index} \\ \text{of treated plot})}}{\text{root-knot index of untreated plot}} \times 100$$

The control effect of 100% means a perfect control. The results are shown in Table 8.

TABLE 8

| | Concentration of the active ingredient (ppm) | Control effect (%) |
|---|---|---|
| Compound No. | | |
| 3 | 10 | 100 |
| 5 | 25 | 100 |
| 6 | 25 | 100 |
| Comparison A | 50 | 0 |

Note
1. The compounds correspond to those given in Table 10.
2. The compound used for comparison is the same as in Table 1.

The following Synthesis Example specifically illustrates a process for producing the compound of general formula (III) which is an intermediate for the production of the compound of this invention.

SYNTHESIS EXAMPLE 1

(Compound No. III-1)

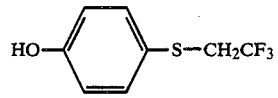

With stirring in an atmosphere of nitrogen, 110 g of anhydrous potassium carbonate was added to a solution composed of 51 g of 4-hydroxybenzenethiol and 250 ml of dimethylformamide. Furthermore, 112 g of 2,2,2-trifluoroethyl p-toluenesulfonate was added at a temperature of 25° to 30° C. The mixture was stirred at the same temperature for 3 hours, then at 30° to 40° C. for 4 hours, and finally at 50° C. for 6 hours. After cooling, the solution was poured into 2 liters of water, and concentrated hydrochloric acid was added at a temperature lower than 20° C. to adjust the pH of the solution to 3. The resulting oily product was extracted with toluene. The toluene layer was washed with water, and stirred together with 600 ml of a 10% aqueous solution of potassium hydroxide. The aqueous layer was separated, and hydrochloric acid was added at a temperature lower than 20° C. to adjust the pH of the aqueous layer to 2. The resulting oily product was extracted with toluene. The toluene layer was separated, washed with water, and then dried over anhydrous sodium sulfate. The toluene was evaporated, and the residue was distilled under reduced pressure to give 68 g of the desired 4-(2,2,2-trifluoroethylthio)phenol. b.p. 102°-105° C./0.8 mmHg.

By nearly the same method as above, the phenol derivatives of this invention represented by general formula (III), as shown in Table 9, were produced.

TABLE 9

| Compound No. | Starting material | Starting material | Product of general formula (III) |
|---|---|---|---|
| III-2 | 2,2,2-Trifluoroethyl p-toluenesulfonate | 2-Hydroxybenzenethiol | 2-(2,2,2-Trifluoroethylthio)-phenol (63-65° C./0.7 mm Hg) |
| III-3 | 2,2,3,3-Tetrafluoropropyl p-toluenesulfonate | 4-Hydroxybenzenethiol | 4-(2,2,3,3-Tetrafluoropropylthio)phenol (117-119° C./0.5 mm Hg) |
| III-4 | 2,2,3,3-Tetrafluoropropyl p-toluenesulfonate | 2-Hydroxybenzenethiol | 2-(2,2,3,3-tetrafluoropropylthio)phenol |
| III-5 | 2,2,3,3,3-Pentafluoropropyl p-toluenesulfonate | 4-Hydroxybenzenethiol | 4-(2,2,3,3,3-Pentafluoropropylthio)phenol |

The following Synthesis Examples specifically illustrate the process for producing the organophosphate derivatives of general formula (I) of this invention which are the active compounds in accordance with this invention.

SYNTHESIS EXAMPLE 2

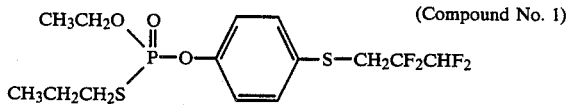

(Compound No. 1)

Four grams of 4-(2,2,3,3-tetrafluoropropylthio)-phenol and 1.9 g of triethylamine were dissolved in 60 ml of toluene. To the solution was added dropwise 3.56 g of O-ethyl-S-propylthiophosphate chloride at 10° to 20° C. The mixture was stirred at 50° C. for 6 hours. The reaction mixture was cooled, washed successively with 2% hydrochloric acid, a 2% aqueous solution of potassium hydroxide, and water, and dried over anhydrous sodium sulfate. Under reduced pressure, toluene was evaporated, and the residue was distilled under reduced pressure to give 3 g of the desired O-ethyl-S-propyl-O-[4-(2,2,3,3-tetrafluoropropylthio)phenyl]thiophosphate.

Boiling point: 156°-158° C./0.2 mmHg
$n_D^{20}$: 1.5041

SYNTHESIS EXAMPLE 3

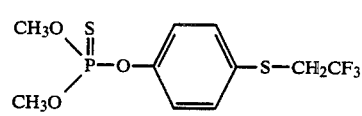

(Compound No. 2)

To a mixture composed of 4.16 g of 4-(2,2,2-trifluoroethylthio)phenol, 2.8 g of anhydrous potassium carbonate and 50 ml of methyl ethyl ketone was added dropwise 3.17 g of O,O-dimethylthiophosphate chloride with stirring at 20° to 25° C. The solution was stirred at 50° to 55° C. for 6 hours, and under reduced pressure, methyl ethyl ketone was evaporated. Toluene (80 ml) and 80 ml of water were added. The toluene layer was separated, washed successively with a 2% aqueous solution of potassium hydroxide and water, and dried over anhydrous sodium sulfate. Under reduced pressure, toluene and low-boiling substances were evaporated to give 5 g of the desired O,O-dimethyl-O-[4-(2,2,2-trifluoroethylthio)phenyl]thiophosphate.

$n_D^{20}$: 1.5163

By nearly the same methods as in Synthesis Examples 2 and 3, the organophosphate derivatives of general formula (I) shown in Table 10 were produced.

TABLE 10

$$\begin{array}{c} R^1-O \quad Y \\ \phantom{R^1-O}\diagdown \| \\ \phantom{R^1-O \quad Y}P-O-\!\!\!\left\langle\!\!\!\begin{array}{c}\phantom{x}\end{array}\!\!\!\right\rangle\!\!-\!S(O)_n-CH_2R^3 \\ \phantom{R^1-O}\diagup \\ R^2-X \end{array}$$

| Compound No. | X | Y | $R^1$ | $R^2$ | $R^3$ | n | Bonding position | Physical constant |
|---|---|---|---|---|---|---|---|---|
| 3 | S | O | —$C_2H_5$ | n-$C_3H_7$ | —$CF_3$ | 0 | 4- | bp. 157-160° C./0.8 mmHg $n_D^{20}$ 1.5050 |
| 4 | S | O | —$C_2H_5$ | n-$C_3H_7$ | —$CF_3$ | 0 | 2- | bp. 142-146° C./0.4 mmHg |
| 5 | S | S | —$C_2H_5$ | n-$C_3H_7$ | —$CF_3$ | 0 | 4- | $n_D^{20}$ 1.5357 |
| 6 | O | S | —$C_2H_5$ | —$C_2H_5$ | —$CF_3$ | 0 | 4- | $n_D^{20}$ 1.5021 |
| 7 | O | S | —$C_2H_5$ | —$C_2H_5$ | —$CF_3$ | 2 | 4- | $n_D^{20}$ 1.5075 |
| 8 | S | O | —$C_2H_5$ | sec-$C_4H_9$ | —$CF_3$ | 0 | 4- | $n_D^{20}$ 1.5055 |
| 9 | S | O | —$C_2H_5$ | —$C_2H_4OC_2H_5$ | —$CF_3$ | 0 | 4- | $n_D^{20}$ 1.5045 |
| 10 | NH | S | —$C_2H_5$ | iso-$C_3H_7$ | —$CF_3$ | 0 | 4- | $n_D^{20}$ 1.5106 |
| 11 | O | S | —$C_2H_5$ | —$C_2H_5$ | —$CF_2CHF_2$ | 0 | 4- | $n_D^{20}$ 1.4985 |
| 12 | S | S | —$C_2H_5$ | n-$C_3H_7$ | —$CF_2CHF_2$ | 0 | 4- | $n_D^{20}$ 1.5296 |

TABLE 10-continued

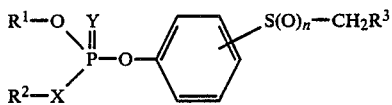

| Compound No. | X | Y | R¹ | R² | R³ | n | Bonding position | Physical constant |
|---|---|---|---|---|---|---|---|---|
| 13 | S | O | —$C_2H_5$ | sec-$C_4H_9$ | —$CF_2CHF_2$ | 0 | 4- | $n_D^{20}$ 1.5030 |

Note
The "bonding position" shows the position to which the group —S(O)—$CH_2R^3$ is bonded on the phenyl group.

SYNTHESIS EXAMPLE 4

O,O-diethyl-O-[4-(2,2,2-trifluoroethylsulfonyl)-phenyl]thiophosphate, compound No. 7 of the invention shown in Table 10, can be easily obtained also by heating 1 mole of O,O-diethyl-O-[4-(2,2,2-trifluoroethylthio)phenyl]thiophosphate, compound No. 6 of the invention, in acetic acid together with 2.0 to 2.2 moles of aqueous hydrogen peroxide at 30° to 50° C. for 2 hours; or by an ordinary oxidizing reaction in which compound No. 6 is refluxed for 2 hours with 2.0 to 2.2 moles of meta-chloroperbenzoic acid in chloroform. The physical constant of the product is $n_D^{20}$=1.5075 as shown in Table 10.

SYNTHESIS EXAMPLE 5

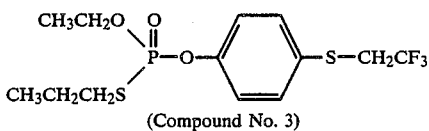

(Compound No. 3)

A mixture of 3.7 g of potassium O-ethyl-O-[4-(2,2,2-trifluoroethylthio)phenyl]thiophosphate, 1.4 g of propyl bromide and 30 ml of acetonitrile was stirred at 50° to 60° C. for 3 hours. Acetonitrile was evaporated, and water was added to the residue. The mixture was stirred, and the resulting oily substance was extracted with 50 ml of toluene. The toluene layer was washed with two 50 ml. portions of a saturated aqueous solution of sodium bicarbonate and then with water. The organic layer was separated, and dehydrated over anhydrous sodium sulfate. Toluene was evaporated, and the residue was distilled under reduced pressure to give 2.8 g of the desired O-ethyl-S-propyl-O-[4-(2,2,2-trifluoroethylthio)phenyl]thiophosphate.

Boiling point: 157°-160° C./0.8 mmHg
$n_D^{20}$: 1.5050

It is understood that the specification and examples are illustrative but not limitative of the present invention and that other embodiments within the spirit and scope of the invention will suggest themselves to those skilled in the art.

What is claimed is:

1. An organophosphate derivative of the formula

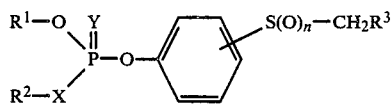

in which
X is O, S or NH,
Y is O or S,
R¹ is a lower alkyl group,
R² is a lower alkyl group or a lower alkoxy-lower alkyl group,
R³ is a fluoro-substituted lower alkyl group, and
n is 0 or 2.
the S(O)$_n$—$CH_2R^3$ substituent being attached to the 2- or 4-position of the phenyl ring.

2. A method of combating pests which comprises applying to the pests or a pest habitat a pesticidally effective amount of an organophosphate derivative according to claim 1.

3. An organophosphate derivative according to claim 1, in which
R¹ is alkyl with 1 to 4 carbon atoms,
R² is alkyl with 1 to 4 carbon atoms, or alkoxyalkyl with 1 to 4 carbon atoms in each of the alkyl and alkoxy moieties, and
R³ is alkyl with 1 to 4 carbon atoms which is substituted by 1 to 4 flourine atoms.

4. An organophosphate derivative according to claim 1, in which
R¹ is methyl or ethyl,
R² is methyl, ethyl, n.- or i.-propyl, s.-butyl or ethoxyethyl,
R³ is trifluoromethyl or 1,1-difluoro-2,2-difluoroethyl, and
S(O)$_n$$CH_2$—$R^3$ is in the 2- or 4-position of the phenyl ring.

5. An organophosphate derivative according to claim 4, in which n is O.

6. An organophosphate derivative according to claim 4, in which the S(O)$_n$$CH_2$—$R^3$ group is in the 4-position of the phenyl ring.

7. An organophosphate derivative according to claim 1, wherein such derivative is O-ethyl-S-propyl-O-(4-(2,2,3,3-tetrafluoropropylthio)phenyl)thiophosphate of the formula

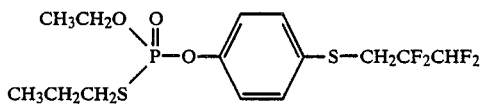

8. An organophosphate derivative according to claim 1, wherein such derivative is O,O-dimethyl-O-(4-(2,2,2-trifluoroethylthio)phenyl)thiophosphate of the formula

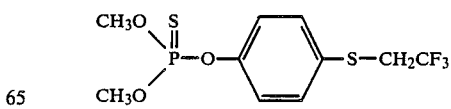

9. An organophosphate derivative according to claim 1, wherein such derivative is O-ethyl-S-propyl-O-(4-

(2,2,2-trifluoroethylthio)phenyl)thiophosphate of the formula

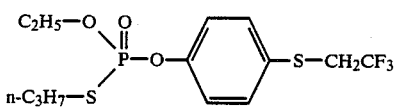

10. An organophosphate derivative according to claim 1, wherein such derivative is O-ethyl-S-propyl-O-(2-(2,2,2-trifluoroethylthio)phenyl)thiophosphate of the formula

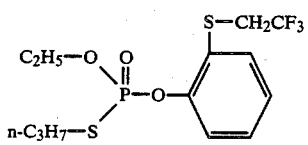

11. An organophosphate derivative according to claim 1, wherein such derivative is O-ethyl-S-propyl-O-(4-(2,2,2-trifluoroethylthio)phenyl)dithiophosphate of the formula

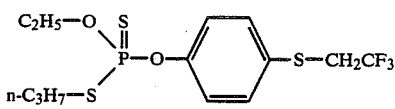

12. An organophosphate derivative according to claim 1, wherein such derivative is O,O-diethyl-(4-(2,2,2-trifluoroethylthio)phenyl)dithiophosphate of the formula

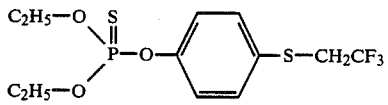

13. An organophosphate derivative according to claim 1, wherein such derivative is O-ethyl-N-isopropyl-O-(4-(2,2,2-trifluoroethylthio)phenyl)amidothiophosphate of the formula

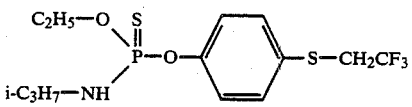

14. A pesticidal composition comprising a pesticidally effective amount of an organophosphate derivative according to claim 1 in admixture with a diluent.

15. The method according to claim 2, wherein such organophosphate derivative is
O-ethyl-S-propyl-O-(4-(2,2,3,3-tetrafluoropropylthio)phenyl)thiophosphate,
O,O-dimethyl-O-(4-(2,2,2-trifluoroethylthio)phenyl)thiophosphate,
O-ethyl-S-propyl-o-(4-(2,2,2-trifluoroethylthio)phenyl)thiophosphate,
O-ethyl-S-propyl-O-(2-(2,2,2-trifluoroethylthio)phenyl)thiophosphate,
O-ethyl-S-propyl-O-(4-2,2,2-trifluoroethylthio)phenyl)dithiophosphate,
O,O-diethyl-(4-(2,2,2-trifluoroethylthio)phenyl)dithiophosphate, or
O-ethyl-N-isopropyl-O-(4-(2,2,2-trifluoroethylthio)phenyl)amidothiophosphate.

* * * * *